United States Patent [19]

Nescio

[11] 3,932,386

[45] Jan. 13, 1976

[54] SODIUM 6-(L-AMINOCYCLOHEXANE CARBOXAMIDO)PENICILLANIC ACID

[75] Inventor: John J. Nescio, West Chester, Pa.

[73] Assignee: American Home Products Corporation, New York, N.Y.

[22] Filed: June 18, 1973

[21] Appl. No.: 370,909

[52] U.S. Cl.............................. 260/239.1; 424/271
[51] Int. Cl.² ..................................... C07D 499/44
[58] Field of Search .................................. 260/239.1

[56] References Cited

UNITED STATES PATENTS

| | | | |
|---|---|---|---|
| 2,684,363 | 7/1954 | Wachtel et al.................. | 260/239.1 |
| 3,194,802 | 7/1965 | Alburn et al..................... | 260/239.1 |
| 3,262,928 | 7/1966 | Granater.......................... | 260/239.1 |
| 3,472,841 | 10/1969 | Johnson et al................... | 260/239.1 |
| 3,553,201 | 1/1971 | Clark et al....................... | 260/239.1 |
| 3,674,776 | 7/1972 | Long et al........................ | 260/239.1 |

FOREIGN PATENTS OR APPLICATIONS 980,240  1/1965  United Kingdom

Primary Examiner—Nicholas S. Rizzo
Attorney, Agent, or Firm—Richard K. Jackson

[57] ABSTRACT

Crystalline, anhydrous sodium cyclacillin is produced by the reaction of a primary, secondary or tertiary lower alkylamine salt of 6-(1-aminocyclohexanecarboxamido)penicillanic acid and a sodium alkanoate in the presence of an anhydrous solvent system comprising a lower alkanol and a saturated hydrocarbon.

11 Claims, No Drawings

SODIUM 6-(L-AMINOCYCLOHEXANE CARBOXAMIDO)PENICILLANIC ACID

BACKGROUND OF THE INVENTION

The production of sodium cyclacillin has been fraught with problems due to the form of the product which is either non-isolable in conventional filtration equipment or so hygroscopic as to be very difficult to handle in processing subsequent to its recovery from the reaction medium. Heretofore, only the hydrated forms of sodium cyclacillin could be isolated satisfactorily in conventional filtration equipment. However, the hydrated forms of sodium cyclacillin are extremely hygroscopic, presenting a relatively non-uniform product which impares quantitative measuring techniques of sampling, weighing, dispensing, and the like, as well as presenting storage stability problems. Previous attempts to produce anhydrous sodium cyclacillin by employing anhydrous conditions throughout the processing procedure have afforded a material which was non-isolatable in conventional filtration equipment due to its particle size and/or form.

DESCRIPTION OF THE INVENTION

In accordance with this invention, there is provided a process for the production of sodium 6-(1-aminocyclohexanecarboxamido)penicillanate which comprises reacting an anhydrous amine salt of 6-(1-aminocyclohexanecarboxamido)penicillanic acid with a sodium salt of an alkanoic acid in an anhydrous solvent system of an alkanol containing 2 or 3 carbon atoms and a saturated hydrocarbon containing from 5 to 8 carbon atoms. The product, sodium cyclacillin, forms an additional aspect of this invention as a free-flowing, white, crystalline, substantially anhydrous, readily filterable compound which is less hygroscopic and more stable than sodium cyclacillin produced by other processes.

Applicant has discovered that by performing the reaction of a sodium alkanoate with an anhydrous amine salt of cyclacillin in an anhydrous solvent system consisting of an alkanol containing 2 or 3 carbon atoms and a saturated hydrocarbon containing from 5 to 8 carbon atoms, the product is substantially anhydrous, of low hygroscopicity and, surprisingly, crystalline in form, rendering it readily filterable by conventional means and weighable (dispensable) with accuracy in subsequent processing procedures as in the preparation of dosage forms. In fact, the product of this invention may be dried in a circulating air oven to obtain it in substantially anhydrous form, a property not found in sodium cyclacillin containing water of hydration in its molecular structure as is produced by other techniques. In addition, the potency of the product of this invention is retained for a considerably longer time than that of sodium cyclacillin prepared by other techniques The reactant amine salt of anhydrous cyclacillin may be any amine derived from a primary, secondary or tertiary alkylamine in which each alkyl group independently contains from 1 to 4 carbon atoms. The preferred amine salts are derived from isopropylamine, diethylamine and triethylamine.

The alkanoic acid employed as the sodium salt reactant may be any alkanoic acid salt that is soluble in the reaction medium. It is preferred to employ an alkanoic acid containing from 6 to 14 carbon atoms of which 2-ethylhexanoic acid is the most preferred acid due to its cost, availability, and solubility characteristics.

The reaction proceeds smoothly at a temperature from $-10°$ to $40°C$. while a temperature from $0°$ to $30°C$. is preferred. Thus, depending upon the specific reactants and solvent system employed, the reaction may be conducted at about room temperature with slight modification for optimization of any specific reaction system.

The solvent system employed in the process of this invention is a mixture of a saturated hydrocarbon and an alkanol. The saturated hydrocarbon may contain from 5 to 8 carbon atoms and be from the alkane of cycloalkane series. Thus, pentane, hexane, heptane, octane, and the corresponding cyclic hydrocarbons and mixtures thereof are applicable in the process of this invention. The alkanol may contain 2 or 3 carbon atoms, namely, ethanol, propanol and isopropanol.

The solvent system is initially made up in an approximate 1:1 ratio of saturated hydrocarbon to alkanol. Additional amounts of the saturated hydrocarbon may be added to the reaction medium after crystallization is initiated, to increase the crop of crystals. Thus, the ratio of saturated hydrocarbon to alkanol at the final stage of the reaction is within the range of from 1–4:1 parts, respectively. Seed crystals, prepared by conventional means such as removal of a portion of the reaction medium, cooling, scratching the side of the vessel, etc., are beneficially introduced into the reaction medium after addition of the sodium alkanoate has begun, to initiate crystallization.

The crystalline, substantially anhydrous sodium cyclacillin product contains no water-of-crystallization although it is hygroscopic and will gain weight slowly by absorption of atmospheric moisture. However, the hygroscopicity of this substantially anhydrous sodium cyclacillin is much less than that of non-crystalline sodium cyclacillin. Isolation and packaging handling of the sodium cyclacillin of this invention are greatly simplified because of negligible water pick-up in normal processing as sharply contrasted with non-crystalline sodium cyclacillin. Package stability because of low water pick-up assures a better quality product reaching the consumer.

EXAMPLE I

Sodium 6-(1-Aminocyclohexanecarboxamido)penicillanate

To 300 ml. of anhydrous ethanol is added 100 g. (0.293 mole) of anhydrous 6-(1-aminocyclohexanecarboxamido)penicillanic acid followed by 23.6 g. (0.322 mole) of diethylamine at about 20°C. with stirring. After stirring of one half hour, the solution is clarified by filtration through diatomaceous earth and the filter cake is washed with 50 ml. of a 1:1 mixture of hexane and anhydrous ethanol. The resulting solution of diethylamine 6-(1-aminocyclohexanecarboxamido)penicillanate is diluted with 500 ml. of hexane. To the slowly stirred solution of the diethylamine salt is gradually added over a thirty minute period at from about 20°–23°C., a solution of sodium 2-ethylhexanoate (prepared by the reaction of 16.6 g. (0.309 mole) of sodium methoxide with 46.5 g. (0.322 mole) of 2-ethylhexanoic acid in 200 ml. of a 1:1 mixture of anhydrous ethanol and hexane at a temperature maintained below 30°C. followed by filtration and the addition of 15 ml. of a 1:1 mixture of hexane and anhydrous ethanol to wash the filter). After addition of about 75 ml. of the solution of sodium 2-ethylhexanoate, seed material of sodium 6-(1-aminocyclohexanecarboxamido)penicillanate separately formed, is added to the solution to initiate crystallization. After complete addition of the sodium 2-ethylhexanoate solution, stirring is continued for ½ hour, 200 ml. of hexane is added over a 30 minute period and stirring is continued for another half hour at from about 20°–23°C.

The white, crystalline product is collected by filtration, washed by stirring in a mixture of 160 ml. of hexane and 40 ml. of anhydrous ethanol, filtered, and finally washed with a mixture of 80 ml. of hexane and 20 ml. of anhydrous ethanol. After drying in a vacuum oven at 45°–50°C., the product amounts to 84.0 g. (79 per cent of theory); moisture content 0.27 per cent; potency by bioassay, 99 per cent.

a calculated amount of water based on a Karl Fischer determination was added to de-silylate and precipitate the product. After vacuum drying, the sodium cyclacillin retained water.

C

A dilute solution of sodium hydroxide was added slowly to a slurry of anhydrous cyclacillin in water to a pH of 9.3. The solution was freeze-dried for 48 hours to obtain the product.

Samples of sodium cyclacillin, prepared by the three preceding methods and the process of Example I, were compared for potency, moisture content, crystallinity, storage stability and hygroscopicity. The results of these direct comparisons are presented in the table:

| Test Compared | Example 1 | A | B | C |
|---|---|---|---|---|
| Iodometric Assay mcg./mg. (theory 941) | 914 | 904 | 883 | 908 |
| Bioassay mcg./mg. (theory 941) | 941 | 981 | 912 | 945 |
| Water Content (KF) | 0.5% | 2.4% | 1.8% | 3.8% |
| Crystallinity by X-ray diffraction | crystalline | non-crystalline | non-crystalline | non-crystalline |
| Potency after Storage at 75°C. for 1 week (iodometric) | 804 | 570 | 649 | 534 |
| Potency after storage at 75°C. for 1 week (Bioassay) | 819 | 432 | 660 | 390 |
| Moisture Pickup at 79% R.H. | | | | |
| 1 hour | 0.5% | 1.1% | 5.7% | 3.6% |
| 2 hours | 0.8% | 8.3% | 9.0% | 7.0% |
| 4 hours | 1.4% | 12.8% | 15. % | 11.7% |
| 6 hours | 4.7% | 12.2% | 17.5% | 14.6% |

The X-ray diffraction pattern for the product presented the following values in degrees for 2θ: 6.7*; 10.8; 13.5; 16.0; 16.9*; 17.3*; 19.4*; 22.2; 23.3; 23.8; 27.6; 28.7; 29.3; 30.2; 24.1, in which the asterisk denotes the strongest peaks in the pattern.

For comparative purposes, sodium cyclacillin was also prepared by the following three methods:

A 6-(1-Aminocyclohexanecarboxamido)penicillanic acid (122 g.; 0.36 mole) followed by 32.6 g. (0.45 mole) of diethylamine is added to 840 ml. of acetonitrile with stirring, and the resulting solution is filtered. In a separate vessel, 15.1 g. (0.38 mole) of sodium hydroxide pellets is added to a mixture of 55 g. (0.38 mole) of 2-ethylhexanoic acid, 300 ml. of acetonitrile and 48 ml. of water with stirring. After solution is attained, the warm solution is clarified by filtration.

The solution containing sodium 2-ethylhexanoate is added to the solution of the diethylamine salt of the penicillin over 20 minutes at 20°–25°C. After stirring at room temperature for ½ hour and then at 0°–5°C. for ½ hour, the white sodium salt is collected by filtration and dried in a vacuum oven at 45-50°C.

B

Following the procedure of German Offenlegungsschrift 2,026,508, Example 3, anhydrous cyclacillin was silylated with trimethylchlorosilane in tetrahydrofuran with triethylamine present. After removing the triethylamine hydrochloride by filtration, the filtrate was concentrated under vacuum and dissolved in diethyl ether. The ether solution was added to a tetrahydrofuran-diethyl ether solution of sodium 2-ethylhexanoate and These tests indicate that the process of this invention produces a crystalline, less hygroscopic and more stable product than alternate procedures. The products of procedures A, B and C presented no X-ray diffraction pattern indicative of crystallinity.

The following examples illustrate the production of sodium cyclacillin under analogous reaction conditions to afford the product of this invention in substantially identical form to that of Example I.

EXAMPLE II

The procedure of Example I was repeated except that the final crystallization was carried out at 0°–3°C.; yield, 87.6 g. (82 percent of theory); moisture content, 0 percent; potency by bioassay, 98 percent.

EXAMPLE III

The procedure of Example I was repeated replacing the diethylamine with 19.0 g. (0.32 mole) of isopropylamine; yield, 83.2 g. (79 percent of theory); moisture content, 0.14 percent; bioassay, 98 percent.

EXAMPLE IV

To 300 ml. of anhydrous ethanol is added 100 g. of anhydrous 6-(1-aminocyclohexanecarboxamido)-penicillanic acid followed by 59.3 g. (0.586 mole) of triethylamine. After stirring for one hour, the solution is clarified by filtration through diatomaceous earth and a sterilizing filter, and the filter cake is washed with 50 ml. of a mixture of hexane and anhydrous ethanol. The resulting solution of triethylamine 6-(1-aminocyclohexanecarboxamido)penicillinate is diluted with 500 ml. of hexane. To this slowly stirred solution is gradually added over a 30-minute period at ambient temperature, a solution of sodium 2-ethylhexanoate (prepared by the reaction of 16.6 g. of sodium methoxide with 46.5 g. of 2-ethylhexanoic acid in 200 ml. of 2 1:1 mixture of anhydrous ethanol and hexane at a temperature maintained below 30°C. followed by sterile filtration and the addition of 15 ml. of a mixture of hexane and anhydrous ethanol to wash the filter). After addition of about 75 ml. of the solution of 2-ethylhexanoate, seed material of sodium 6-(1-aminocyclohexanecarboxamido)penicillanate, is added to initiate crystallization. The crystallization and isolation is the same as that used in Example I; yield, 91.0 g. (86 percent of theory); moisture content, 0.2 percent; bioassay, 98 percent.

EXAMPLE V

The procedure of Example I was repeated replacing the hexane with cyclohexane throughout the process; yield, 48.4 g. (45 percent of theory); moisture content, 0.3 percent; bioassay, 100 percent.

What is claimed is:

1. Crystalline sodium 6-(1-aminocyclohexanecarboxamido)-penicillanate.
2. A process for the production of crystalline sodium 6-(1-aminocyclohexanecarboxamido)penicillanate which comprises reacting an anhydrous amine salt of 6-(1-aminocyclohexanecarboxamido)penicillanic acid with a sodium salt of an alkanoic acid in an anhydrous solvent system of a lower alkanol containing 2 or 3 carbon atoms and a saturated hydrocarbon containing from 5 to 8 carbon atoms.
3. The process of claim 2 in which said amine salt of 6-(1-aminocyclohexanecarboxamido)penicillanic acid is selected from the group consisting of primary, secondary and tertiary alkylamine salts in which each alkyl group independently contains from 1 to 4 carbon atoms.
4. The process of claim 3 in which said amine salt is the 6-(1-aminocyclohexanecarboxamido)penicillanic acid isopropyl amine salt.
5. The process of claim 3 in which said amine salt is the 6-(1-aminocyclohexanecarboxamido)penicillanic acid diethylamine salt.
6. The process of claim 3 in which said amine salt is the 6-(1-aminocyclohexanecarboxamido)penicillanic acid triethylamine salt.
7. The process of claim 2 in which said alkanoic acid contains from 6 to 14 carbon atoms.
8. The process of claim 7 in which said alkanoic acid is 2-ethylhexanoic acid.
9. The process of claim 2 in which said anhydrous solvent system contains a final volume ratio of saturated hydrocarbon to alkanol within the range of from 1-4:1 parts, respectively.
10. The process of claim 9 in which said solvent system consists of hexane and ethanol.
11. The process of claim 9 in which said solvent system consists of cyclohexane and ethanol.

* * * * *